United States Patent [19]

Yoshimura et al.

[11] Patent Number: 5,292,654
[45] Date of Patent: Mar. 8, 1994

[54] MUTANT EPO RECEPTOR AND USES THEREFOR

[75] Inventors: Akihiko Yoshimura, Somerville; Gregory D. Longmore, Brookline; Harvey Lodish, Brookline, all of Mass.

[73] Assignee: Whitehead Institute for Biomedical Research, Cambridge, Mass.

[21] Appl. No.: 626,923

[22] Filed: Dec. 13, 1990

[51] Int. Cl.[5] .................. C12Q 1/68; C12P 21/06; C12N 5/00; C07H 15/12; C07H 17/00; C07K 3/00; C07K 13/00; C07K 15/00; C07K 17/00

[52] U.S. Cl. .................. 435/240.2; 435/6; 435/69.4; 435/69.5; 435/69.6; 536/23.5; 530/350; 530/351; 935/10; 935/11; 935/66; 935/70; 935/72

[58] Field of Search ............... 435/6, 69.4, 69.5, 69.6, 435/240.2; 530/350, 351, 397; 536/27; 935/10, 11, 66, 70, 72

[56] References Cited

PUBLICATIONS

D'Andrea et al (Dec. 1990) The Cytoplasmic Region of the Erythropoietin Receptor . . . Blood 76:89(A) Abstract 348.

Jones et al. (1990 Jul.) Human Erythropoietin Receptor . . . Blood 76:31–35.

D'Andrea, A. D., et al., *Mol. Cell. Biol.* 11(4):1980–7. (Apr. 1991).

Yoshimura, A. et al., *Nature* 348 647–649 (Dec. 13, 1990).

Quelle, D. E. and Wojchowski, D. M., *Proc. Natl. Acad. Sci. USA* 88: (11):4801–5 (Jun. 1, 1991).

D. Andrea, A D., et al *Cell* 57:277–285 (Apr. 21, 1989).

*Primary Examiner*—Christine M. Nucker
*Assistant Examiner*—David R. Preston
*Attorney, Agent, or Firm*—Hamilton, Brook, Smith & Reynolds

[57] ABSTRACT

A mutant erythropoietin receptor of mammalian origin which is hypersensitive to erythropoietin, DNA encoding the mutant erythropoietin receptor and uses therefor. An assay method for identifying compounds which mimic erythropoietin is also disclosed.

3 Claims, 4 Drawing Sheets

MUTANT EPO RECEPTOR AND USES THEREFOR

DESCRIPTION

1. Funding

Work described herein was supported by funding from the Nakatomi Health Science Foundation (Saga, Japan), and the National Institutes of Health.

2. Background

Erythropoietin (EPO) is a glycoprotein hormone of relative molecular mass 34,000 (M 34K) that induces proliferation and differentiation of erythroid progenitor cells. Erythropoietin stimulates mitotic activity of erythroid progeniter cells and triggers transformation of erythrocyte colony forming units into proerythroblasts. Until recently, little was known about the mechanism by which erythropoietin acts to induce erythroblast proliferation and differentiation or the nature of the erythropoietin receptor (EPO-R) located on erythroblast surfaces. Following the cloning of the murine EPOR complementary DNA, D'Andrea and co-workers developed a cell-culture system to study the proliferative action of the receptor. D'Andrea, A. D. et al., Cell 57:277-285 (1989). Expression of the EPOR cDNA was shown to allow interleukin-3-(IL-3)-dependent hematopoietic Ba/F3 cells to grow in the presence of erythropoietin. Li, J. P. et al., Nature 343:762-764 (1990); and Yoshimura, A. et al., Proc. Natl. Acad. Sci. U.S.A. 87:4139-4143 (1990). Similarly, Ba/F3 cells can be switched to IL-2-dependent growth by expression of the IL-2 receptor β-chain (IL-2RB). Itch et al., Science 247:324-327 (1990). Regions of the cytoplasmic domain of the IL-2R,6, IL-3 receptor, and EPOR are similar (D'Andrea, A. D. et al., Cell 58:1023-1024 (1989); Itch et al., Science 247:324-327 (1990); and Baron, J. F. Biochem. Biophy. Res. Commun. 164:788-795 (1989)), and thus, these receptors may share similar signal transducing pathway(s). As a result of this work, considerably more is now known about the intact EPO-R.

DISCLOSURE OF THE INVENTION

The present invention relates to a mutant erythropoietin receptor (EPOR) of mammalian origin, a nucleotide sequence (DNA or RNA) encoding the mutant EPOR (mutant EPOR-encoding DNA or RNA), and host cells which contain a mutant EPOR-encoding nucleotide sequence and in which mutant EPOR can be produced. The invention further relates to a method of producing mutant EPOR, cell lines containing mutant EPOR-encoding DNA or RNA, antibodies specific for mutant EPOR, a method of producing antibodies specific for mutant EPOR and an assay useful for identifying compounds which mimic the action of EPO or interact with EPOR. In the assay, a mutant EPOR which is more responsive to EPO than is the wild type EPOR (i.e., a hypersensitive EPOR) is used. Because of the enhanced sensitivity or receptivity of the mutant EPOR (relative to that of the wild type (WT) or native (EPOR), the assay method of the present invention makes it possible to identify compounds which bind less weakly, relative to the ligand, than can be identified using the wild type EPOR.

As described herein, mutant cells lines which exhibit responsiveness to erythropoietin different from that shown by cells expressing wild type EPOR have been obtained. In particular, two types of cell lines have been identified: one which is more responsive to erythropoietin than are cells expressing the wild-type EPOR (nEPOR), but cannot grow in the absence of growth factor and one which grows in the absence of hematopoietic growth factors. As is further described herein, constitutive receptors have been isolated from mutant cells lines and characterized. One constitutive receptor (designated sEPOR) is normal size and the other (designated ctEPOR) is truncated at the C- terminus. In one constitutive EPOR (designated tEPOR), a 193 base-pair (bp) deletion spanning the 3' coding and noncoding region resulted in replacement of the normal C-terminal 42 amino acids with alanine and leucine. In a second constitutive EPOR (designated cEPOR), there is one point mutation (a transition from C to T at nucleotide 484), which caused one substitution (arginine to cysteine) in the exoplasmic domain of EPOR at codon 129 of the predicted N-terminus. The constitutive EPOR designated ctEPOR has the point mutation present in cEPOR and the 193 bp deletion evident in tEPOR.

These mutations have been shown to be responsible for the mutant phenotype of the cell lines, as is also described herein. That is, it has been shown that the arginine to cysteine point mutation evident in cEPOR is sufficient to induce factor-independent growth and that deletion of the C-terminal 42 amino acids enhances sensitivity to erythropoietin for growth.

BRIEF DESCRIPTION OF THE DRAWINGS

In FIGS. 1A–C, numbers of the amino acids and codon positions are indicated from the predicted N-terminus. The transmembrane domains (TM), initiation (ATG) and termination (TAG or TGA) codons are indicated. Single lines represent non-translated regions of the messenger RNA.

DETAILED DESCRIPTION OF THE INVENTION

Mutant EPORs have been isolated from Ba/F3 cells infected with vectors expressing the EPOR cDNA. The cDNAs encoding the mutant EPORs have been isolated and the difference(s) between the mutant EPOR-encoding DNA and the corresponding region(s) of the wild-type or native EPOR DNA have been determined. In addition, the amino acid sequence of the mutant EPOR encoded by mutant EPOR DNA has been determined and compared with the amino acid sequence of wild-type EPOR protein.

Figures 1A, 1B, 1C:
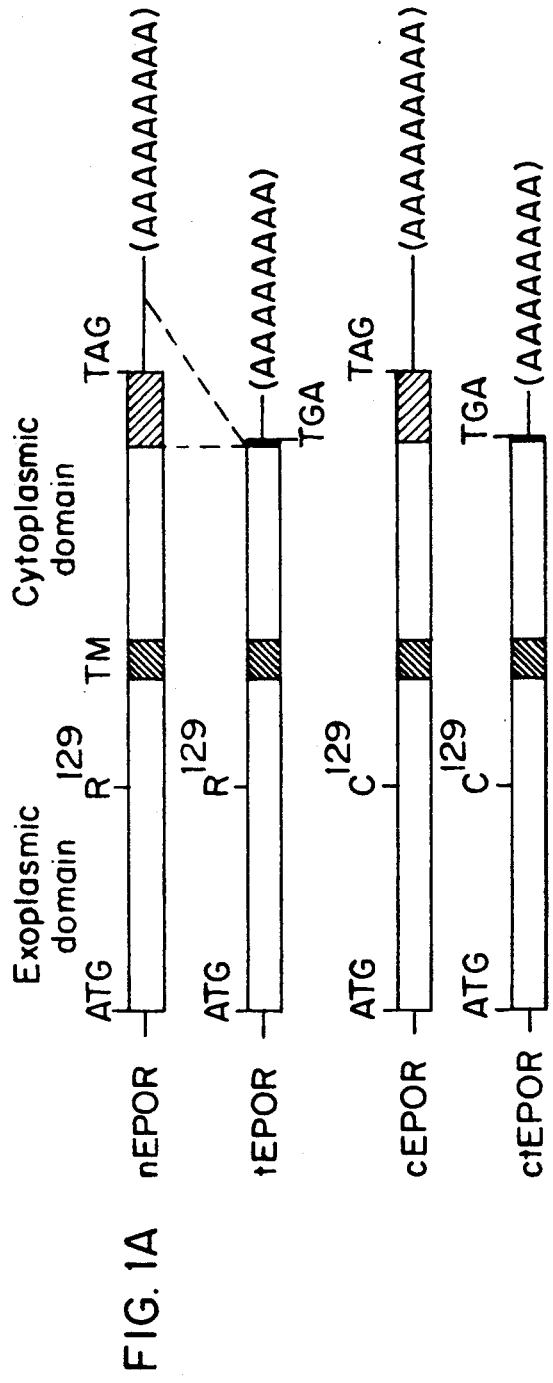
FIG. 1A is a schematic representation of wild-type and mutant EPOR cDNAs.
FIG. 1B shows the deletion mutation in tEPOR.
FIG. 1C shows the point mutation in the mutant cEPOR cDNA.

As a result, as described herein, mutant EPOR proteins which differ from wild-type EPOR in amino acid sequence and function or activity are available, as are nucleotide sequences encoding them and methods in which each is useful, such as assay methods. In addition, antibodies which recognize mutant EPOR can also be produced, using known techniques, and, in turn, used in assay and diagnostic methods. In one embodiment of the present invention, a mutant EPOR, referred to as a hypersensitive EPOR, which is more receptive or sensitive to EPO than is the wild type EPOR, is used. For example, a mutant EPOR which differs from the wild type EPOR in that it is truncated can be used. In particular, as described herein, a hypersensitive mutant (designated tEPOR) has been obtained. cDNA encoding tEPOR has a 193 base-pair deletion which spans the 3' coding and noncoding region (from $^{1424}G$ to $^{1616}G$) which results in replacement of the normal C-terminal 42 amino acids (i.e., the 42 amino acids present in wild type EPOR) with alanine (A) and lysine (L). This mutant, which is represented in FIG. 1B (also SEQ ID NO: 6-10 is useful in an assay for identifying compounds which mimic EPO and is particularly useful because of its increased sensitivity to EPO.

The following is a description of isolation of mutant cell lines which express mutant EPOR (i.e., EPOR which differs from wild-type EPOR by a deletion, substitution or addition of at least one amino acid and responds to erythropoietin in a manner different from that in which wild-type EPOR responds), demonstration that the mutant phenotypes result from the mutations and characterization of the mutant EPOR.

Some receptors containing tyrosine-kinase domains can be constitutively activated by point mutations and deletions. Such mutations are frequently found in retroviral oncogenes (for example, v-fms and v-neu), whose origins are normal cellular genes. However, no constitutively activated mutants of any member of the cytokine receptor family have been detected to date. As described herein, mutant EPORs have been isolated from Ba/F3 cells infected with retroviruses expressing the erythropoietin receptor cDNA. Li, J. P. et al., Nature 343:762-764 (1990). This strategy was used because as the virus replicates in the packaging cells (Itch, N. et al., Science 247:324-327 (1990); and Danos, O. and R. C. Mulligan, Proc. Natl. Acad. Sci. U.S.A. 86:6460-6464 (1988)), spontaneous mutations in the EPOR gene may occur. Isolation of mutant cell lines is described in detail in Example 1. The mutant EPOR cell lines contain DNA which differs from DNA encoding wild-type EPOR by at least one nucleotide and, as a result, encodes EPOR protein which differs by at least one amino acid from the amino acid sequence of wild-type EPOR protein.

Selection of cell lines by gradual decreases in the concentration of erythropoietin in the medium resulted in two classes of mutant cell lines: one mutant cell line is more responsive to erythropoietin than are cells expressing the wild-type receptor (nEPOR), but cannot grow in the absence of growth factor. This cell line (tEPOR) has a C-terminal truncation in the EPOR. The other mutant cell line type grows in the absence of any hematopoietic growth factors. Two constitutive receptors were isolated from these cells: one which is of normal size (sEPOR) and one which is truncated in the C-terminus (ctEPOR). The wild-type (nEPOR) cDNA and mutant EPOR (tEPOR, cEPOR, ctEPOR) cDNAs are shown in FIG. 1.

Mutation sites in the integrated receptor cDNA were identified as described in Example 1. In tEPOR, a 193 base-pair (bp) deletion spanning the 3' coding and noncoding region (from $^{1,424}G$ to $^{1,016}G$) resulted in replacing the normal C-terminal 42 amino acids with alanine (A) and leucine(L) (FIG. 1C also SEQ ID NO: 6-10). In cEPOR there was one point mutation - a transition from C to T at nucleotide 484 causing one substitution in the exoplasmic domain, from arginine (R) to cysteine (C) at codon 129 of the predicted N-terminus (after signal sequence processing) (FIG. 1C also SEQ ID NO: 11-14). D'Andrea, A. D. et al., Cell 57:277-285 (1989). In ctEPOR, exactly the same point mutation as in cEPOR and the same deletion as in tEPOR was found. Thus, one type of activating mutation, a C-terminal truncation in the cytoplasmic domain of the EPOR, renders the receptor hyper-responsive to erythropoietin, but is insufficient to induce hormone-independent growth or tumorigenicity. The other type of mutation, a point mutation, retards intracellular transport and turnover of the receptor. These alterations in metabolism and tumorigenicity caused by the EPOR with activating point mutations are similar to those observed in erythropoietin-independent activation of the wild type EPOR by association with gp55, the Friend spleen focus-forming virus glycoprotein. Li, J. P. et al., Nature, 343:762-764 (1990); and Yoshimura, A. et al., Proc. Natl. Acad. Sci. U.S.A. 87:4139-4143 (1990).

Figure 3:
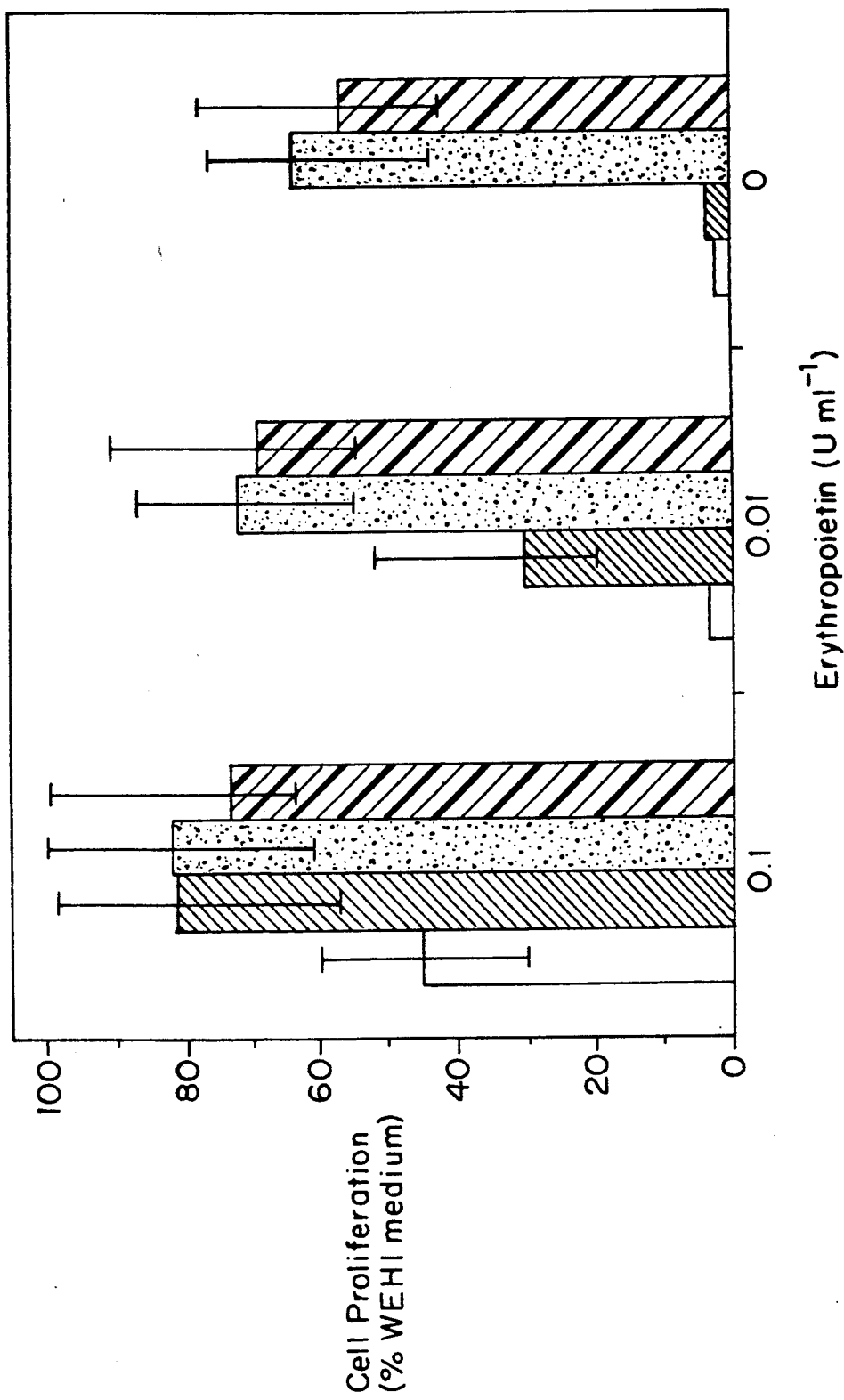
FIG. 3 is a graphic representation of growth of Ba/F3-EPOR transfectants in different concentrations of erythropoietin.

To show that these mutations are responsible for the mutant phenotype, the isolated mutant EPOR cDNAs were subcloned into the mammalian expression vector pXM (D'Andrea, A. D. et al., Cell 57:277-285 (1989)) and introduced into Ba/F3 cells (FIG. 3). Transfection with tEPOR cDNA resulted in cell lines able to grow in one-tenth the physiological concentration of erythropoietin (0.01 unit ml$^{-1}$), but still unable to grow in the absence of erythropoietin. Only transfection of cEPOR or ctEPORcDNAs generated factor-independent cell lines. Thus the arginine to cysteine point mutation is enough to induce factor-independent growth, and deletion of the C-terminal 42 amino acids enhances the sensitivity to erythropoietin for growth.

Factor-independent Ba/F3 cells can also form tumours in syngeneic mice (Example 3 and the Table). Parental Ba/F3 cells, or erythropoietin-dependent tranformants (nEPOR cells or tEPOR cells) were not tumorigenic, but hormone-independent cEPOR cells and nEPOR-gp55 cells (created by infection of nEPOR cells with SFFV[5]) generate tumours in mice. This suggests that constitutively activated receptors have tumorigenic potential.

Figure 2A:
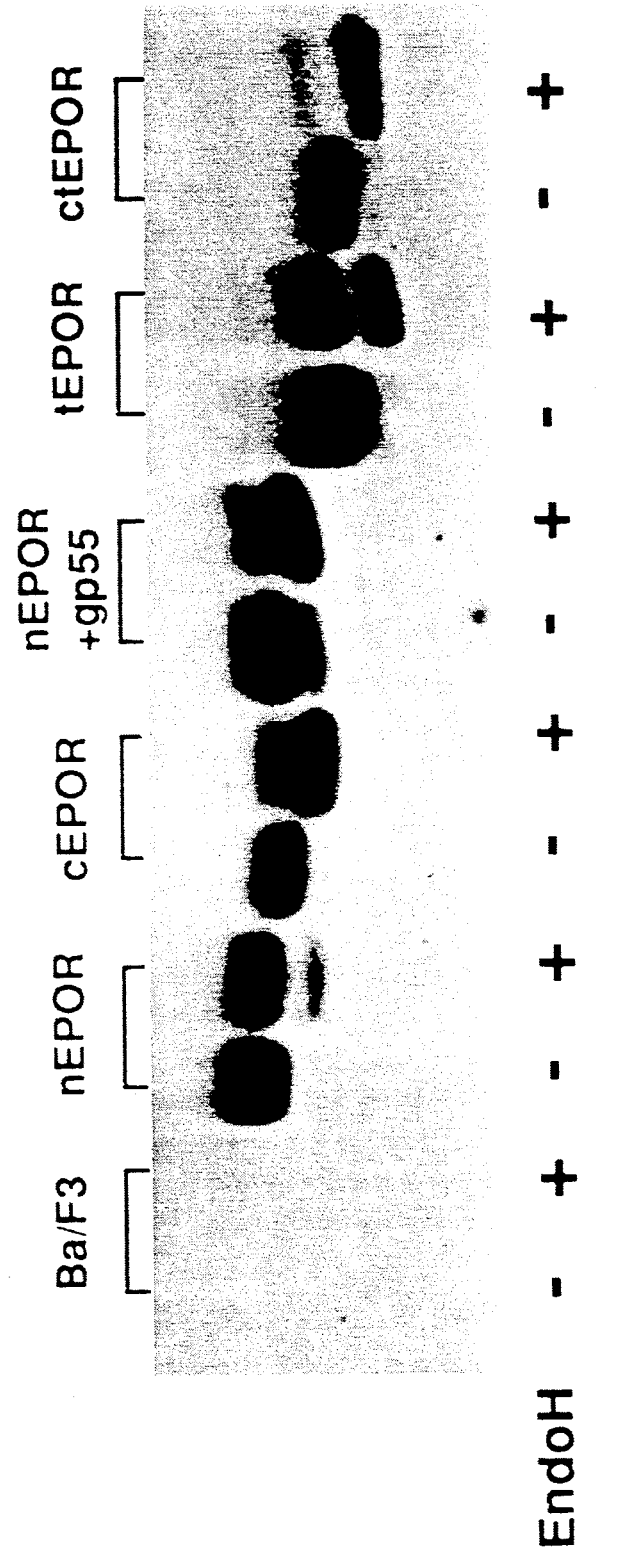
FIG. 2A shows expression of EPOR in parental Ba/F3 cells and cells expressing nEPOR, cEPOR, tEPOR and ctEPOR
Figure 2B:
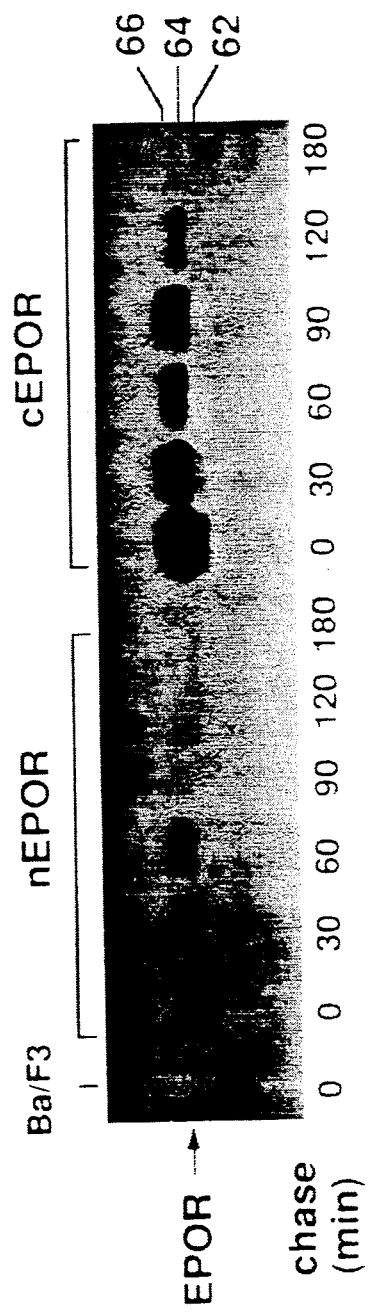
FIG. 2B shows expression of nEPOR and cEPOR in transfected cells by pulse-chase analysis.

The point mutation in the exoplasmic domain affects receptor metabolism. Wild-type EPOR is synthesized as a major 64K endoglycosidase H(EndoH)-sensitive species and a minor 62K unglycosylated form. Fukunaga, R. et al., Cell 61:341-350 (1990)). The 64K form is processed to a 66K mature EndoH-resistant form, a fraction of which is on the cell surface. All three forms are, degraded very quickly, with a half-life of about 40 minutes (FIG. 1B). The tEPOR has similar processing and half-life. At steady-state, 60-80% of the nEPOR and tEPOR polypeptides are the EndoH-resistant mature species. By contrast, cEPOR and ctEPOR cells contain very little EndoH-resistant receptor (FIG. 2A). Pulse-chase experiments show little processing of the cEPOR to a 66K, EndoH-resistant species, and the half-life the cEPOR was longer than that of the nEPOR (FIG. 2B). Such retention of the receptor polypeptide in the endoplasmic reticulum was also seen in the hormone-independent cell line expressing nEPOR and gp55 (nEPOR-gp55) (FIG. 2A and Yoshimura, A. et al., Proc. Natl. Acad. Sci. U.S.A. 87:4139-4143 (1990)). These data suggest that a similar activating conformational change of the EPOR can occur by a point mutation or through binding of gp55. However, it was shown that neither the codon-129 mutation nor association with gp55 affects ligand-binding affinity of the cell surface receptor.

Activation of the EPOR by a point mutation in the expoplasmic domain is quite reminiscent of that of c-fms, the receptor for macrophage colony stimulating factor (M-CSF-1). Woolford, L. et al., *Cell* 55:966-977 (1988); Roussel, M. F. et al., *Cell* 55:97-98 (1988); Roussel et al., *Nature* 325:549-552 (1987); and Roussel, M. F. et al., *Oncogene* 5:25-30 (1990). A single point mutation in the exoplasmic domain activates the tyrosine kinase of c-fms, perturbs receptor transport and turnover, does not affect ligand binding and results in transformation. Also, modifications at the C- terminal region of c-fms increase ligand responsiveness, but are themselves insufficient to induce transformation.

Recent studies suggest that autocrine activation of the cytokine receptors are involved in leukaemogenesis. Schrader, J. W. and R. M. Crapper, *Proc. Natl. Acad. Sci. U.S.A.* 80:6892-6896 (1983); Schrader, J. W., *Rev. Immun.* 4:205-230 (1986); Taga, T. and Y. Kishimoto, *Curr. Op. Cell Biol.* 2:174-180 (1990); and Lang, R. A. et al., *Cell* 43:532-542 (1985). The data presented herein raise the possibility that mutational activation of the EPOR or other cytokine receptors could be a mechanism for overriding normal hormonal control of proliferation of haematopoietic cells.

As a result of the work described herein, mutant EPOR are now available. A mutant EPOR which is more responsive to EPO (grows in or proliferates in response to a concentration of EPO less than that in which wild type or native EPOR grows or proliferates) than is the wild type (naturally occurring) EPOR can be used, for example, to identify compounds which mimic EPO. Use of a hypersensitive EPOR in assaying for EPO-like compounds is particularly advantageous because lower concentrations of compounds being tested can be used (i.e. concentrations lower than must be used in an assay using wild type EPOR). As a result, concentrations of test compounds which are not toxic to cells or do not otherwise adversely affect the cells can be used; because of the heightened sensitivity of the mutant EPOR to EPO, a compound which mimics EPO will be detected at a lower concentration than is possible with wild type EPO.

For example, a mutant EPOR such as tEPOR can be used to test compounds for their EPO-like characteristics. As described herein, tEPOR is at least 10-fold more sensitive to EPO than wild type EPOR (see Example 4 and FIG. 3). In one embodiment of an assay to identify compounds which mimic EPO (EPO-like compounds), mutant EPOR-encoding DNA is expressed in host cells (such as hematopoietic Ba/F3 cells) which are IL-3 dependent and able to grow in the presence of erythropoietin. In such a cell-culture system, the proliferative action of the receptor can be assessed. (See, for example, Li, J. P. et al., *Nature*, 343:762-764 (1990) and Yoshimura, A. et al., *Proc. Natl. Acad. Sci., U.S.A.*, 87:4139-4143 (1990), the teachings of which are incorporated herein by reference.) A compound to be tested for EPO-like activity is added to the cell culture system. The cells are maintained under conditions appropriate for host cell growth. The effect on host cell (hematopoietic cell) proliferation is assessed by, for example, determining tritiated thymidine uptake or by colorimetric MTT assay, in which a dye reduced by the mitochondria in growing cells is detected. Those compounds which are shown to mimic EPO can then be analyzed for characteristics which contribute to or determine their ability to be recognized or bound by EPOR. The information gained in this way can be used to design new compounds which mimic EPO or to modify existing compounds such that they mimic EPO or have enhanced EPO-like activity.

Although the assay for compounds which mimic EPO has been described with specific reference to tEPOR, which is a murine mutant EPOR, it is to be understood that other hypersensitive mutant EPOR, which can be identified using the method described herein or by another technique, can also be used. Other mutant EPOR can be of mammalian origin (e.g., murine, human, bovine). The mutation introduced into the wild type nucleotide sequence to produce mutant EPOR (i.e., the difference between the wild type sequence and the mutant sequence) can be an addition, deletion or substitution, which results, in turn, in addition, deletion or substitution of at least one amino acid of the expressed EPOR. As used herein, the term mutant EPOR which is hyperresponsive to EPO includes all mammalian EPOR which differ in amino acid sequence from the corresponding EPOR and which grow in or proliferate in response to a concentration of EPO less than that in which the corresponding wild type grows or proliferates. For example, as shown by tEPOR, the difference between the mutated EPOR and wild type EPOR can be encoded by DNA in which a deletion spans the 3' coding and noncoding region, resulting in replacement in the EPOR of the C-terminal amino acids present in the wild type EPOR. The deletion may be shorter or longer than that present in DNA encoding tEPOR, resulting in a shorter or longer altered region of the mutant EPOR. Other mutant EPORs can be identified using the techniques described herein.

As also described herein, mutational activation of the EPOR might be a mechanism for overriding normal hormonal control of proliferation of haematopoietic cells. It is possible that mutations, such as the point mutation and point-mutation/truncation change seen (cEPOR and ctEPOR, respectively) are associated with cell transformation. If this is the case, detection of such mutations using known methods (such as oligonucleotide probes and antibodies specific for mutation-containing EPOR protein) could be useful in the diagnosis of conditions such as leukemia, preleukemia syndrome and polycythemia vera.

EXAMPLE 1

Isolation of Mutant Cell Lines

Isolation of mutant cell lines was carried out as follows: A retroviral vector containing the wild-type EPOR cDNA (pSF.ER) was packaged and amplified in a mixture of helper cell lines, psi-cre and psi-crip. Li, J-P et al., *Nature,* 343:762-784 (1990); Danos, O. and R. C. Mulligan, *Proc. Natl. Acad. Sci., U.S.A.,* :6460-6464 (1988). Infected Ba/F3 cells ($1 \times 10^7$) were selected by incubating cells for 7 days in medium containing a physiological concentration of erythropoietin (0.1 U ml$^{-1}$ or 10 pM). All clones eventually isolated in this selection medium expressed nEPOR. Cells were further selected by incubating cells in 0.01 U ml$^{-1}$ erythropoietin for 14 days. At this concentration, cells expressing the wild-type receptor cannot grow. All 12 clones obtained in this selection medium contained tEPOR, as judged by lack of reactivity with an anti-C-terminal antibody (Li, J. P. et al., *Nature* 343:762-784 (1990)) and by molecular size (FIG. 2A). One of these clones, ctEPOR, was found to grow in the absence of any growth factor. Another factor-independent cell clone, cEPOR, was isolated by culturing Ba/F3 cells infected with the same virus sample in the absence of erythropoietin using a similar procedure (FIG. 2A).

EXAMPLE 2

Cloning and Sequencing of the Mutant EPOR cDNA

Mutant EPOR cDNA was cloned and sequences as follows: Integrated full-length EPOR cDNA was directly amplified from genomic DNA of wild type and cEPOR cells by using polymerase chain reaction (VCR) (11) primers N1 (5' AAGGTACCTGAAGC-TAGGGCTGGATCA-3' (SEQ ID NO: 1): bases -18-1) and C1 (5'-GGGAATTCGGCTGGAGTC-CTAGGAGCAG-3': (SEQ ID NO: 2): bases 1,561-1,542), then cloned into vectors M13mp18, M13mp19 and pXM using EcoRI and KpnI cloning sites. For tEPOR and ctEPOR, two partially overlapping cDNA fragments that covered the full-length cDNA were obtained by using two PCR primer sets: N1 and P11(5'-GCAGAGTCCGGCGGTGGG-3': (SEQ ID NO: 3): bases 859-842), and also P3 (5'-GACCACC-CAGATCCGATATG-3': (SEQ ID NO: 4), bases 546-565) and P826 (5'-AAGCTTAACATT-GCAAGGCT-3': (SEQ ID NO: 5): bases 1,654-1,638). The former fragments were cloned into M13 vectors using KpnI and NheI sites, and the latter fragments cloned into the vector as two separate fragments after digestion with HindIII. Single stranded DNA was obtained and sequenced using synthetic oligonucleotide primers according to Sanger et al. Schrader, J. W. and R. M. Crapper, *Proc. Natl. Acad. Sci. U.S.A.* 80:6892–6896 (1983). Constructs of tEPOR and ctEPOR in pXM were made from pXM-nEPOR or pXM-cEPOR cDNA by replacing the HindIII-EcoRI fragment (corresponding to the C-terminal region of EPOR cDNA) with the HindIII-EcoRI fragment of the tEPOR cDNA cloned in M13 double-stranded DNA.

EXAMPLE 3

Expression of EPOR

Parental Ba/F3 cells were cultured in 10% WEHI-conditioned medium as a source of IL-3. Yoshimura, A. et al., *Proc. Natl. Acad. Sci. U.S.A.* 87:4139–4143 (1990). The nEPOR cells and tEPOR cells were cultured in 0.1 U ml$^{-1}$ and 0.01 U ml$^{-1}$ EPO, respectively. The cEPOR, etEPOR and nEPOR-gp55 cells (Li, J. et al., *Nature* 343:762–764 (1990); and Yoshimura, A. et al., *Proc. Natl. Acad. Sci. U.S.A.* 87:4139–4143 (1990)) were cultured in normal RPMI medium. Cells were retrovirus infectants isolated as described in Example 1. Membranes from cells were digested with or without EndoH, separated by SDS-PAGE in 7.5% polyacrylamide gels, and immunoblotted with an antibody against a peptide corresponding to the N-terminal 14 amino acids of the EPOR as described previously. Li, J. et al., *Nature* 343:762–764 (1990); and Yoshimura, A. et al., *Proc. Natl. Acad. Sci. U.S.A.* 87:4139–4143 (1990). Results are shown in FIG. 2A. Similar results were obtained from plasmid pXM transfectants (data not shown). Cells expressing nEPOR or cEPOR (retroviral transfectants) were metabolically labelled with [$^{35}$S]methionine for 30 minutes and chased for the indicated periods (see FIG. 2B). Samples were immunoprecipitated with the above antibody against the EPOR and subjected to 7.5% SDS-PAGE and fluorography. Yoshimura, A. et al., *Proc. Natl. Acad. Sci. U.S.A.* 87:4139–4143 (1990). Results are shown in FIG. 2B.

EXAMPLE 4

Growth of Ba/F3-EPOR transfectants in different concentrations of erythropoietin Wild-type or mutant EPOR cDNAs were subcloned into pXM as described in Example 1. Ba/F3 cells ($1 \times 10^7$) were transfected by electroporation with 20 ug of the plasmids linearized with XbaI. Cells were further cultured in medium supplemented with 10% WEHI-conditioned medium. After 24 hours further incubation, cells were washed and cultured in 0.25 U ml$^{-1}$ of erythropoietin for 5 days to select cells expressing an EPOR. Individual clones were isolated by limited dilution. These clones were expanded in 10% WEHI-conditioned medium and were tested for growth factor sensitivity. Cells (1,000 per well) were cultured in the presence of 10% WEHI-conditioned medium, 0.1 U ml$^{-1}$ erythropoietin, 0.01 U ml$^{-1}$ erythropoietin, or no added growth factor for 3 days. The number of living cells was estimated by colorimetric MTT assay. Li, J. et al., *Nature* 343:762–764 (1990). Growth of cells from each clone in the presence of differing amounts of erythropoietin or with no added growth factor was normalized to growth in the presence of 10% WEHI-conditioned medium. Results are presented graphically in FIG. 3. As shown, Ba/F3-EPOR transfectants expressing wild type EPOR (nEPOR) and Ba/F3-EPOR transfectants expressing mutant EPOR (tEPOR, cEPOR, ctEPOR) grew in 0.1 U ml$^{-1}$ EPO. In 0.01 U ml$^{-1}$ EPO, however, transfectants expressing wild type EPOR (nEPOR) did not survive, but those expressing mutant EPOR did. The bars represent an average of all clones of each type tested (nEPOR, open bar, 7 clones: tEPOR, diagonal lines, 8 clones; cEPOR, speckled 11 clones; ctEPOR, multi-striped, clones) and error bars define the range of proliferation values (maximum and minimum values).

EXAMPLE 5

Tumor Formation in Syngeneic Mice Injected with Mutant EPOR Expressing Cells

TABLE 1

Tumorigenicity of Ba/F3 clones expressing EPOR

| cDNA | Tumours in mice injected with clones derived from: | |
|---|---|---|
| | Plasmid (pXM) transfection | Retroviral infections |
| mock | 0/5 | N.D. |
| nEPOR | 0/4 | 0/4 |
| tEPOR | N.D. | 0/6 |
| cEPOR | 6/6 | 6/6 |
| nEPOR-gp55 | N.D. | 6/8 |

N.D., not determined.

Wild-type and mutant EPOR-expressing Ba/F3 cells (retrovirus infectants isolated as described in Example 1 and pXM transfectants as described in Example 2) were injected into syngeneic Balb/c mice less than 12 weeks old. Mice received 0.5 Gy(500 rads) of γ-irradiation 24 hours before cell challenge. Cells ($3-5 \times 10^6$ per mouse) were washed with serum-free medium, resuspended in Hanks' balanced salt solution and injected into mice subcutaneously. Mice were observed for 2–3 months for signs of palpable or visible tumours at the site of injection. Tumorigenic cell lines gave rise to visible masses with a short latency after injection (2-3 weeks) which was nonregressing and malignant. Representative mice injected with nontumorigenic cell lines were killed and autopsies performed to ensure tumours had not developed.

EQUIVALENTS

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. DNA encoding a mutant erythropoietin receptor having an alteration of the wild-type murine erythropoietin receptor selected from the group consisting of:
   a) replacement of the C-terminal 42 amino acids with alanine-leucine;
   b) replacement of the arginine at codon 129 with cysteine; and
   c) replacement of the C-terminal 42 amino acids with alanine-leucine and replacement of the arginine at codon 129 with cysteine.

2. A host cell containing a mutant erythropoietin receptor having an alteration of the wild-type murine erythropoietin receptor selected from the group consisting of:
   a) replacement of the C-terminal 42 amino acids with alanine-leucine;
   b) replacement of the arginine at codon 129 with cysteine; and
   c) replacement of the C-terminal 42 amino acids with alanine-leucine and replacement of the arginine at codon 129 with cysteine.

3. Mutant erythropoietin receptor having an alteration of the wild-type erythropoietin receptor selected from the group consisting of:
   a) replacement of the C-terminal 42 amino acids with alanine-leucine;
   b) replacement of the arginine at codon 129 with cysteine; and
   c) replacement of the C-terminal 42 amino acids with alanine-leucine and replacement of the arginine at codon 129 with cysteine.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AAGGTACCTG AAGCTAGGGC TGCATCA    2 7

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear.

( x i ) SEQUENCE DESCRIPTION: SEQ ID NO:2:

GGGAATTCGG CTGGAGTCCT AGGAGCAG    2 8

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCAGAGTCCG GCGGTGGG    1 8

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GACCACCCAC ATCCGATATG    2 0

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AAGCTTAACA TTGCAAGGCT    2 0

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..21
        ( D ) OTHER INFORMATION: /product="Portion of wild-type murine EPOR"

( x i ) SEQUENCE DESCRIPTION: SEQ ID NO:6:

```
GGC ATC TCA ACA GAT TAC AGT    21
Gly Ile Ser Thr Asp Tyr Ser
 1                   5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Gly Ile Ser Thr Asp Tyr Ser
 1                   5
```

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

```
TGACCTTGGC CCTCTGAG    18
```

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..21
        ( D ) OTHER INFORMATION: /product="C-terminus of tEPOR"

( x i ) SEQUENCE DESCRIPTION: SEQ ID NO:9:

```
GGC ATC TCA ACA GCC CTC TGAGCAGGA    28
Gly Ile Ser Thr Ala Leu
 1                   5
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Gly Ile Ser Thr Ala Leu
1               5

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..15
        ( D ) OTHER INFORMATION: /product="Internal portion of
            wild-type murine EPOR"

( x i ) SEQUENCE DESCRIPTION: SEQ ID NO:11:

CTG GCG CGC CGG GCA    15
Leu Ala Arg Arg Ala
1               5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Leu Ala Arg Arg Ala
1               5

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..15
        ( D ) OTHER INFORMATION: /product="Internal portion of
            cEPOR"

( x i ) SEQUENCE DESCRIPTION: SEQ ID NO:13:

CTG GCG TGC CGG GCA    15
Leu Ala Cys Arg Ala
1               5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Leu Ala Cys Arg Ala